United States Patent [19]

Dabney

[11] 3,965,895

[45] June 29, 1976

[54] APPARATUS FOR CONTROLLED VOLUME AND RATE ADMINISTRATION OF LIQUIDS

[75] Inventor: William C. Dabney, Oakland, Calif.

[73] Assignee: Cutter Laboratories, Inc., Berkeley, Calif.

[22] Filed: Aug. 21, 1974

[21] Appl. No.: 499,199

[52] U.S. Cl. ............................ 128/214 C; 128/227; 137/592; 141/374; 222/444
[51] Int. Cl.² ........................................ A61M 5/16
[58] Field of Search ......... 128/214 R, 214 C, 214.2, 128/227, 272; 222/444, 450; 141/374; 137/590, 592

[56] References Cited
UNITED STATES PATENTS

| 720,562 | 2/1903 | Castle | 141/374 X |
| 2,700,973 | 2/1955 | Ju | 128/276 |
| 3,216,419 | 11/1965 | Scislowicz | 128/214 C |
| 3,625,211 | 12/1971 | Butler | 128/214 C |
| 3,646,935 | 3/1972 | Holbrook et al. | 128/276 |
| 3,756,237 | 9/1973 | Wilson et al. | 128/227 |
| 3,776,229 | 12/1973 | McPhee | 128/214 C |
| 3,881,640 | 5/1975 | Noble | 222/158 |

FOREIGN PATENTS OR APPLICATIONS

| 1,182,016 | 2/1970 | United Kingdom | 128/214 C |

Primary Examiner—Dalton L. Truluck
Attorney, Agent, or Firm—Gardiner, Sixbey, Bradford & Carlson

[57] ABSTRACT

Apparatus for selective controlled volume and rate administration of parenteral solutions, blood and the like, wherein sight and flow control problems caused by splashing and foaming of fluids having high surface tension such as blood are substantially diminished, and flow rates during different time phases of operation are optimized due to an arrangement of structure providing an increased head pressure on flow of fluid to a measuring chamber.

20 Claims, 5 Drawing Figures

APPARATUS FOR CONTROLLED VOLUME AND RATE ADMINISTRATION OF LIQUIDS

BACKGROUND OF THE INVENTION

Administration sets for delivery of parenteral solutions, blood and the like, have been heretofore available to the medical profession, which included volumetric chambers that allowed accurately measured volumes of solution to be administered to a patient. Volumetric sets of this type are especially essential for delivering discrete small volumes to infants and young children who could not tolerate larger, unregulated volumes of fluids. Volumetric control sets of this type are disclosed in prior U.S. Pat. Nos. 3,216,418 and 3,216,419. With volumetric control sets of this type, precise small volumes of fluid can be delivered but they cannot, however, be used for direct flow from a supply container through the volumetric chamber when such a flow is desired since the fluid can flow faster into the chamber than flow from the chamber so that the chamber will fill completely and tend to leak from the airway.

U.S. Pat. No. 3,625,211 discloses another type of apparatus for providing delivery of a small, precise volume of solution. In the apparatus of this patent, fluid is introduced by means of a special two-way stopcock into the bottom of the volumetric chamber to fill it to the desired volume. The stopcock has a fail-safe configuration so that fluid can be delivered to the patient from the chamber, but never directly from the supply container. The inability of using these prior constructions for a direct fluid flow from a supply container is overcome in the volumetric administration set disclosed in U.S. Pat. No. 3,776,229 by the simple expedient of providing an on-off at the airway. When the airway is closed, the chamber functions as an extension of the conduit joining the chamber to the supply container so that larger volumes of fluid can flow at a pre-set rate into the patient. With the airway valve open, a precise volume can be introduced into the measuring chamber and subsequently delivered to the patient. This apparatus, accordingly, is useful for accomplishing two functions and separate administration sets are not required.

While the apparatus of this latter patent constitutes an improvement over prior apparatus, it has certain drawbacks which are also present in U.S. Pat. Nos. 3,216,418 and 3,216,419. In these prior devices, when fluids with high surface tension, such as blood, flow or drip from the drip tube at the top of the measuring chamber into the chamber, a considerable amount of frothing develops which not only obscures and makes reading of a meniscus difficult or impossible, but frequently a float member of a valve at the bottom of the chamber is rendered inoperative after the blood drains from the chamber. The float member rides on top of the froth and will not seal the discharge opening. Additionally, blood and other solutions falling from the drip tube cause splashing of the liquid which clings to the walls of the chamber and obscures the vision of a technician when reading a meniscus.

Another problem of substantial significance is present in the prior known administration sets, particularly in those sets where the effective head pressure is rather small as a consequence of existence of a somewhat short column of fluid between the top of the supply fluid and the drip tube. If this head pressure is rather low, then the flow rate into the measuring chamber will be unacceptably slow when one desires to fill the chamber to a certain level.

The present invention provides an administration set wherein these problems existing in the prior known apparatus as disclosed in the aforementioned patents have been overcome.

SUMMARY OF THE INVENTION

The present invention provides apparatus for administration of parenteral solutions, blood and the like, operable for selective controlled volume and rate administration. The apparatus substantially eliminates problems arising through splashing and foaming of fluids having high surface tension such as blood which cause sight and flow control problems. This is accomplished by the point of introduction of the fluid from a supply container to the measuring chamber, i.e., to the bottom of the measuring chamber. This arrangement of introduction of the fluid to the measuring chamber also eliminates to a substantial extent deleterious flow rates during different time phases of operation by providing an increased head pressure on fluid flow to the measuring chamber.

Other and additional advantages and features of the invention will be more readily apparent from the following detailed description of embodiments thereof when taken together with the accompanying drawings in which.

Figure 1:
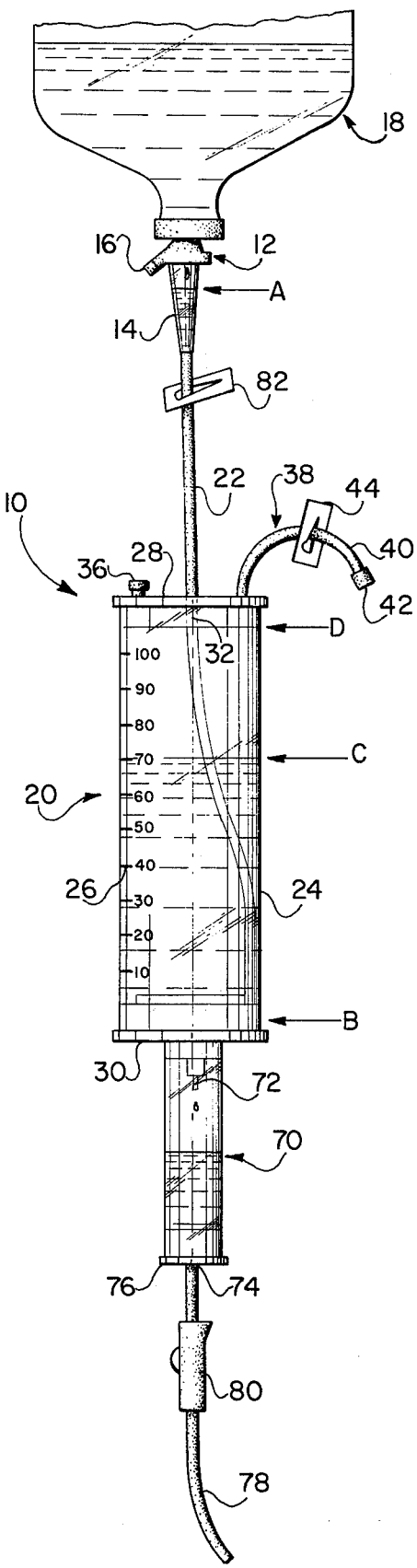
FIG. 1 is a side elevational view of apparatus in accordance with the invention.

The present invention will be more readily understood from the following detailed discussion of embodiments thereof wherein FIG. 1 illustrates a complete set for administration of fluids in accordance with the invention. As shown in FIG. 1, the administration set generally designated 10 includes a hollow spike or entry means 12, having in this case, an integral drip meter 14 and a filtered airway 16. This particular entry means construction 12 is adapted for entry into a rigid fluid supply container 18 and provides for introducing sterile air into the container as fluid is withdrawn.

Measuring chamber 20 is connected to entry means 12 by a flexible conduit 22. The measuring chamber generally designated 20 includes a cylindrical transparent chamber or container 24 having thereon visual calibrated indicia 26. A top wall 28 and a bottom wall 30 are attached to the chamber or container 24 with a centrally located inlet passage 32 being provided in top wall 28 and an outlet passage 34 in bottom wall 30. A sealably pierceable medical entry port 36 is also provided in top wall 28 and a filtered airway generally designated 38 opens through top wall 28 into the chamber and consists of a short piece of tubing 40 and a bacterial filter 42 is incorporated at the outer end of tubing 40. Clamping means 44 is operatively associated with tubing 40 intermediate the ends thereof.

Figure 3:
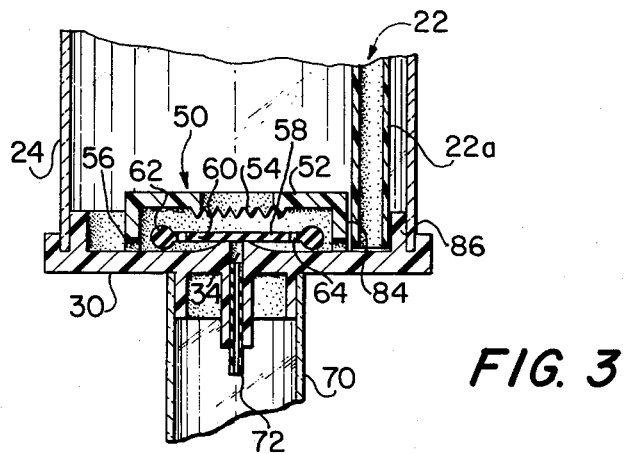
FIG. 3 is a fragmentary enlarged view, partly in section, of one form of valve in the bottom of the measuring chamber; as utilized in the apparatus of FIG. 1.
Figure 4:
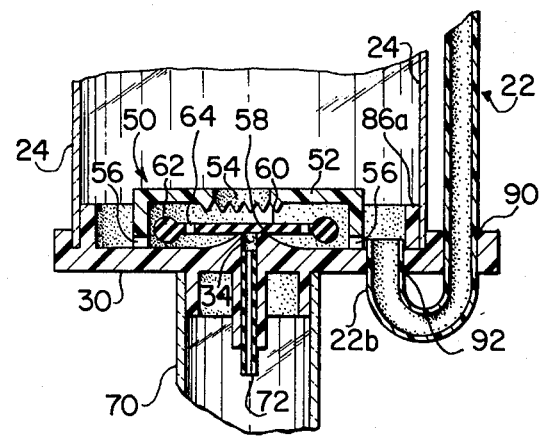
FIG. 4 is a view similar to FIG. 3 disclosing a valve associated with the modified apparatus as shown in FIG. 2.
Figure 5:
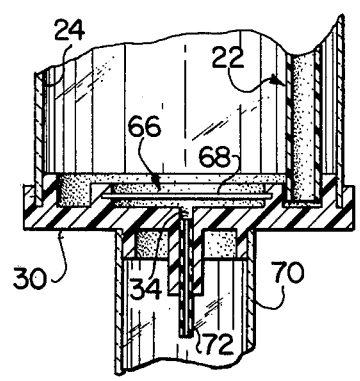
FIG. 5 is a view similar to FIGS. 3 and 4, but disclosing a modification of valve structure adapted to transmit liquids, but not air.

Valve means generally designated 50, as shown in FIGS. 3 and 4, is attached to the interior surface of bottom wall 30. The valve 50 in this embodiment includes a cylindrical cage 52 having in the top thereof a centrally located passage 54 and a plurality of side openings or passages 56 in proximity to the juncture of the cage with bottom wall 30. A floatable resilient diaphragm 58 is positioned within cage 52 and consists in a central imperforate portion 60, a peripheral ring 62 and openings 64. Diaphragm 58 serves to close the outlet passage 34 when fluid level in the chamber drops below passage 54 so that air cannot progress into the patient. This caged float valve construction can be replaced by other types of valves such as, for example, floatable hinged gate valves, not shown, or a membrane valve generally designated 66, as shown in FIG. 5 which includes a porous membrane 68 adapted to transmit liquids, but not air.

A flexible transparent drip chamber 70, generally designated, is connected to bottom wall 30 of chamber 20 and has incorporated therein a centrally located drip tube 72 which at the top communicates with passage 34. An outlet passage 74 is provided in bottom wall 76 of drip chamber 70. A conduit or tube 78 is connected at one end to passage 74 and is adapted at its other end for attachment to a usual needle, not shown, which serves for injecting fluid into a vein of a patient. An adjustable clamp 80 is operatively associated with conduit 78. Clamp means 82 are operatively connected on conduit 22.

An important feature of the invention resides in the manner in which conduit 22 is associated with chamber 24 forming a part of measuring chamber 20. The conduit 22 in the embodiment of FIG. 1 extends to the bottom of measuring chamber 20 and is internally positioned with respect to container 24. As shown in greater detail in FIG. 3, the end 22a of conduit 22 is made secure by wedging it between a vertical wall 84 of cage 52 and an upstanding ledge 86 on bottom wall 30.

Figure 2:
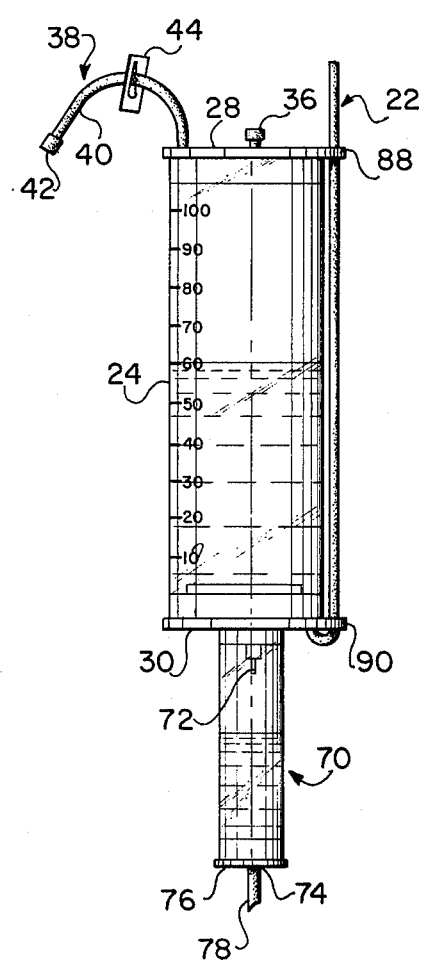
FIG. 2 is a fragmentary side elevational view of apparatus similar to that shown in FIG. 1, but including a modified arrangement of introducing liquid to the measuring chamber.

FIGS. 2 and 4 disclose an embodiment in which tube 22 is positioned externally of chamber 24 and is attached or secured by an apertured ledge or extension 88 on top wall 28 and by means of an apertured extension 90 on bottom wall 30, with the tube end 22b then passing through a passage 92 in bottom wall 30 at a position between cage 52 and upstanding ledge 86a.

In either of these embodiments where the conduit is brought to the bottom of the measuring chamber, either internally or externally, liquid is introduced at the bottom of chamber 20 and splashing and foaming is avoided. In addition, a greater head pressure is generated by the length of the liquid column in the tubing which is the distance between A and B at the start of filling chamber 20 so that liquid will flow in much faster. In apparatus of the prior art as above described, the head pressure is much smaller since the length of the liquid column is shorter, i.e., the distance between A and D so that flow would be slower. The flow rate will, of course, gradually decrease as chamber 20 is filled, but when the liquid level reaches a certain point, as for example, at 70 ml., the head pressure still is greater than in prior art sets since the length between A and C is greater than between A and D.

In U.S. Pat. No. 3,625,211, previously discussed herein, as also in British Pat. No. 438,611, exterior conduits are shown leading from a supply container to the bottom of a measuring chamber. Neither of these latter patents, however, disclose apparatus which can be used in the same manner as the present invention or that shown in U.S. Pat. No. 3,776,229. As regards U.S. Pat. No. 3,625,211, it is noted that the structure of the fail-safe apparatus could not be conveniently used if the valve member 30, 32 therein were replaced by a membrane valve such as at 66, FIG. 5, of the present invention. In order to fill the chamber of this patent, all the fluid must pass up through the membrane and this would be an extremely slow operation since a membrane which is effective is not capable of permitting fast flow rates therethrough. Additionally, if there is an air bubble in the conduit leading to the bottom of the chamber, the membrane being already wet will not pass the air bubble therethrough and incoming liquid flow will be stopped or greatly retarded.

Operation of the apparatus is quite similar to the mode of operation described in U.S. Pat. No. 3,776,229. In using the apparatus for direct through flow from the supply container to the patient, the entry spike is inserted into supply container 18 and clamps 80 and 82 are placed in an open position, and clamp 44 is closed. After liquid has displaced the air in conduit 78, and the adjustments made to achieve the desired liquid levels in drip meter 14 and drip chamber 70, the needle is placed in a vein and the flow rate is adjusted by clamp 80. If it is desired to administer only a discrete volume of solution, then clamp 80 is first closed and clamp 44 is opened, thus allowing solution to fill measuring chamber 20 to a desired level. Clamp 82 is then closed and clamp 80 adjusted so as to provide the desired flow into the patient.

While preferred embodiments have been disclosed and described herein, manifestly minor changes in details of the construction can be effected without departing from the spirit and scope of the invention as defined in and limited solely by the appended claims.

I claim:

1. Apparatus for selective controlled volume administration of a parenteral solution and the like from a fluid supply container, comprising:
   a. a substantially rigid measuring chamber having a top wall and a bottom wall;
   b. said bottom wall having:
      1. an outlet means for dispensing fluid therefrom, and
      2. a fluid inlet means spaced apart from said outlet;
   c. an airway in communication with an opening in said top wall; and
   d. a fluid supply conduit connected to said fluid supply container and extending therefrom continuously and interiorly uninterruptedly to said fluid inlet means and terminating in a discharge end freely opening into said measuring chamber substantially at the interior of bottom wall, whereby splashing and foaming of liquid introduced into said measuring chamber from said supply container is eliminated; and
   e. means fixedly positionally securing the discharge end with respect to said bottom wall.

2. Apparatus as claimed in claim 1, including a drip chamber below said measuring chamber operatively connected therewith.

3. Apparatus as claimed in claim 2, wherein solution injection means are operatively connected to the bottom of said drip chamber.

4. Apparatus as claimed in claim 2, said measuring chamber having an outlet passage in said bottom wall, a drip tube operatively connected to said outlet passage and in open communication within said drip chamber, and valve means attached to the interior surface of said bottom wall above said outlet passage, said valve means being operable to close off said outlet passage when the fluid level in said measuring chamber drops below a predetermined level therein to prevent passage of air distal of said valve means.

5. Apparatus as claimed in claim 4, said valve means including an inverted closed cage attached on said bottom wall and having a top passage therethrough, and a plurality of passages in the base thereof proximate the juncture with said bottom wall, and a floatable resilient diaphragm mounted in said cage, said diaphragm being operable to close off said outlet passage when the fluid level in said chamber drops below said top passage in said cage.

6. Apparatus as claimed in claim 4, wherein said valve means comprises a floatable hinged gate valve.

7. Apparatus as claimed in claim 4, wherein said valve means comprises a membrane valve including a porous membrane attached to and spaced above said bottom wall, said porous membrane being operable to transmit liquids and preclude air passage therethrough.

8. Apparatus as claimed in claim 1, including air control means associated with said airway, said air control means being operable to administer only a discrete volume of solution and for direct through flow from the fluid supply container to a patient.

9. Apparatus as claimed in claim 8, said measuring chamber having a closed top and a sealably pierceable medical entry port on said top.

10. Apparatus as claimed in claim 1, wherein said fluid supply conduit from the connection thereof with said fluid supply container extends downwardly externally of said measuring chamber, with a discharge end thereof extending through an opening at the bottom of said measuring chamber and to said fluid inlet means into said measuring chamber.

11. Apparatus as claimed in claim 10, wherein said outlet means constitutes an outlet opening in said bottom wall, valve means operatively engaging said opening, said valve means including a perforate inverted cage over the opening and having a vertical side wall, said bottom wall further having an upstanding ledge thereon spaced from said vertical side of said cage, said discharge end of said fluid supply conduit being wedged between said vertical side and said upstanding ledge and fixedly positionally securing the discharge end with respect to said bottom wall.

12. Apparatus as claimed in claim 1, wherein said fluid supply conduit from the connection thereof with said fluid supply container extends through said top wall and downwardly in the interior of said measuring chamber, said outlet means constituting an outlet opening in said bottom wall, valve means operatively engaging said opening, said valve means including a perforate inverted cage over the opening and having a vertical side wall, said bottom wall further having an upstanding ledge thereon spaced from said vertical side of said cage, said discharge end of said fluid supply conduit being wedged between said vertical side and said upstanding ledge and fixedly positionally securing the discharge end with respect to said bottom wall.

13. Apparatus for selective controlled volume administration of a parenteral solution and the like from a fluid supply container, comprising:
  a. a substantially rigid measuring chamber having a top wall and a bottom wall;
  b. an airway in communication with an opening in said top wall;
  c. a fluid supply conduit connected to said fluid supply container and from the connection thereof passing through the upper end of said measuring chamber and extending downwardly internally within said measuring chamber to the bottom thereof and terminating in a discharge end opening into said measuring chamber closely proximate said bottom wall, whereby splashing and foaming of liquid introduced into said measuring chamber from said supply container is eliminated,
  d. means fixedly positionally securing the discharge end with respect to said bottom wall, and
  e. fluid outlet means from said measuring chamber.

14. Apparatus as claimed in claim 13, said measuring chamber having a closed top wall, an inlet passage through said top wall, said fluid supply conduit passing through said passage and downwardly into said measuring chamber, and flow control clamping means on said conduit intermediate said fluid supply container and said measuring chamber.

15. Apparatus as claimed in claim 14, said top wall having a sealably pierceable medical entry port, and means for opening and closing said airway.

16. Apparatus as claimed in claim 15, said airway including a tube communicating at one end with the interior of said measuring chamber, filter means including a bacterial filter on the other end of said tube, and control clamping means on said tube.

17. Apparatus for selective controlled volume administration of a parenteral solution and the like from a fluid supply container, comprising:
  a. a substantially rigid measuring chamber having a top wall and a bottom wall;
  b. said bottom wall having:
    1. an outlet passage therein for dispensing fluid therefrom, and
    2. a fluid inlet means spaced apart from said outlet;
  c. an airway in communication with an opening in said top wall;
  d. a drip chamber below said measuring chamber;
  e. a drip tube operatively connected to said outlet passage and in open communication within said drip chamber;
  f. a fluid supply conduit connected to said fluid supply container and extending therefrom continuously and interiorly uninterruptedly to said fluid inlet means and terminating in a discharge end freely opening into said measuring chamber, whereby splashing and foaming of liquid introduced into said measuring chamber from said supply container is eliminated;
  g. valve means attached to the interior surface of said bottom wall above said outlet passage therein to prevent passage of air distal of said valve means;
  h. said valve means including an inverted closed cage, having a vertical wall, and attached on said bottom wall, said cage having a top passage therethrough, and a plurality of passages in the base thereof proximate the juncture with said bottom wall;

i. said valve means further including a floatable resilient diaphragm mounted in said cage, said diaphragm being operable to close off said outlet passage when the fluid level in said chamber drops below said top passage in said cage, defining a predetermined fluid level in said chamber, and serving to prevent passage of air distal of said valve means; and j. said bottom wall of said measuring chamber having an upstanding ledge thereon, the discharge end of said fluid supply conduit being wedged between said vertical wall and said upstanding ledge.

18. Apparatus for selective controlled volume administration of a parenteral solution and the like from a fluid supply container, comprising:
  a. a substantially rigid measuring chamber having a top wall and a bottom wall;
  b. said bottom wall having:
    1. an outlet means for dispensing fluid therefrom, and
    2. a fluid inlet means spaced apart from said outlet;
  c. an airway in communication with an opening in said top wall; and
  d. a fluid supply conduit connected to said fluid supply container and extending therefrom continuously and interiorly uninterruptedly to said fluid inlet means and terminating in a discharge end, said discharge end of said fluid supply conduit extending beyond the bottom of said measuring chamber, and curving and extending upward through and freely opening into the bottom of said measuring chamber, whereby splashing and foaming of liquid introduced into said measuring chamber from said supply container is eliminated.

19. Apparatus as claimed in claim 18, said measuring chamber having a closed top including an apertured extension thereon, a closed bottom wall on said measuring chamber, a passage through said closed bottom wall, said fluid supply conduit extending through the aperture in said top extension and with the end thereof passing through said passage in said closed bottom wall.

20. Apparatus as claimed in claim 18, said measuring chamber having a closed top including an apertured extension thereon, a closed bottom wall on said measuring chamber including an apertured extension thereon, a passage through said closed bottom wall, said fluid supply conduit extending through the aperture in said extensions and with the end thereof passing through said passage in said closed bottom wall.

* * * * *